United States Patent
Aida et al.

(10) Patent No.: US 6,489,273 B1
(45) Date of Patent: Dec. 3, 2002

(54) FRAGRANCE COMPOSITIONS CONTAINING 2-CYCLOHEXYL-1,1-DIMETHYL ETHANOL ESTERS

(75) Inventors: Takashi Aida, Hiratsuki (JP); Hiroyuki Matsuda, Hiratsuki (JP); Tetsuro Yamasaki, Hiratsuki (JP)

(73) Assignee: Takasago International Corporation, Tokyo (JP)

( * ) Notice: Subject to any disclaimer, the term of this patent is extended or adjusted under 35 U.S.C. 154(b) by 14 days.

(21) Appl. No.: 09/723,401

(22) Filed: Nov. 28, 2000

(30) Foreign Application Priority Data

Dec. 17, 1999 (JP) ............................................ 11-359197

(51) Int. Cl.$^7$ ........................ A61K 7/46; C07C 69/025; C11D 3/50
(52) U.S. Cl. ........................ 510/106; 512/22; 560/231
(58) Field of Search ........................ 510/106; 512/22; 568/822; 560/231

(56) References Cited

U.S. PATENT DOCUMENTS

| | | | | |
|---|---|---|---|---|
| 4,006,218 A | * | 2/1977 | Sipos | 424/54 |
| 4,197,318 A | | 4/1980 | Sipos | 424/426 |
| 4,701,278 A | | 10/1987 | Fehr | 252/132 |
| 5,196,329 A | | 3/1993 | Gurley et al. | 435/172.3 |

FOREIGN PATENT DOCUMENTS

EP      1108703    *  6/2001

OTHER PUBLICATIONS

Ch. Vodoz et al., Helvetica Chimica Acta 1950, 33, 1040–1050.*
O. Wallach, Justus Liebigs Annalen Chemie 1912, 394, 362–384.*
Japanese Laid–open Patent Publication of Pat. Application No. 7–238297 Abstract Only.
EP Search Report document for EP 00 40 3555, related case (citing those references listed herein) 2001.
O. Wallach: Justus Liebigs Ann. Chem., vol. 394, 1912, pp. 362–384 XP000926174.
Ch. A. Vodoz et al.: Helv. Chim, Acta, vol. 33, No. 0.2, 1950, pp. 1040–1044.
Database WPI Week 199546, Derwent Publication s Ltd., London, GB AN 1995–354126.
Goldman et al., *J. Pharmacol. Exp. Ther.* 166(1):1–7 (1969).

* cited by examiner

*Primary Examiner*—John Hardee
(74) *Attorney, Agent, or Firm*—Darby & Darby

(57) ABSTRACT

A fragrance, having a 2-cyclohexyl-1,1-dimethyl ethanol derivative represented by formula (1),

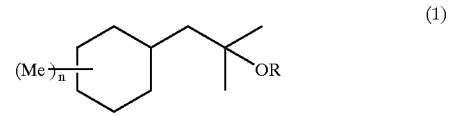

(1)

wherein R represents a hydrogen atom or an acetyl group, Me represents a methyl group and n represents an integer from 0 to 3, provides a very pleasing scent, has excellent stability in a product, and can be mixed well with other fragrances.

10 Claims, No Drawings

FRAGRANCE COMPOSITIONS CONTAINING 2-CYCLOHEXYL-1,1-DIMETHYL ETHANOL ESTERS

BACKGROUND TO THE INVENTION

The present invention relates to a fragrance having a 2-cyclohexyl-1,1-dimethyl ethanol derivative represented by formula (1)

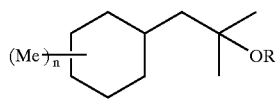
(1)

wherein R represents a hydrogen or an acetyl group, Me represents a methyl group, and n represents an integer from 0 to 3.

In addition, the present invention relates to a fragrance composition containing as an active component a fragrance comprising one or two or more types of 2-cyclohexyl-1,1-dimethyl ethanol derivative represented by the above formula (1). The present invention also relates to an aromatic bleaching composition containing this fragrance composition.

In recent years, with the increasing variety in various perfume products and sanitation products, there are a variety of expectations for fragrances useful for adding scents to these products. Fragrances that provide a pleasant scent, or fragrances that have a very distinctive and agreeable scent, have been sought. Furthermore, there has been increasing demand for fragrances that match the characteristics of individual products. At the same time, in terms of the properties of the fragrance itself, there is a need for fragrances that are chemically stable, while mixing well with other fragrances.

To satisfy these demands, it has always been very important for the fragrance industry to develop and provide fragrance materials that have both individual distinctive characteristics as well as an agreeably pleasing scent.

U.S. Pat. No. 4,006,218 discloses a 2-cyclohexyl-1,1-dimethyl ethanol compound. This compound is used together with an anti-microbial agent, such as cetyl pyridinium chloride, which is commonly used in anti-microbial compositions to increase the anti-microbial action. In addition, Japanese Laid-Open Patent Publication Number 2-31683 discloses 2-cyclohexyl-1,1-dimethyl ethanol as an active component of a pest repellent.

As disclosed in Japanese Examined Patent Publication Number 7-65067, the scent characteristic of 4-cyclohexyl-2-methyl-2-butanol is effective in developing a floral fragrance that is reminiscent of lily of the valley. Methods are disclosed for providing, improving, or modifying the floral fragrance by mixing the compound with other fragrances. Furthermore, Japanese Laid-Open Patent Publication Number 7-238297 discloses 2-cyclohexyl-2-propylesters as fragrance compounds.

However, there are no descriptions of the scent characteristics of 2-cyclohexyl-1,1-dimethylethanol compounds and their acetates and the like. In addition, there are no descriptions of methods for using these compounds as fragrance materials used in adding scent to various perfume products and sanitation materials.

OBJECTS AND SUMMARY OF THE INVENTION

It is an object of the present invention to provide a fragrance material that overcomes the foregoing problems.

It is a further object of the present invention to provide a fragrance material that is very pleasing and satisfies the requirements corresponding to the product characteristics, that has excellent stability in the product, and that can be mixed well with other fragrances.

It is still a further object of the present invention to provide a fragrance composition comprising this fragrance material as an active component.

It is another object of the present invention to provide a method for using this fragrance composition.

As a result of intensive research to attain the above objectives, the present inventors have discovered that 2-cyclohexyl-1,1-dimethyl ethanol derivatives have a pleasing and highly unique scent, are chemically stable, and have excellent harmony with other fragrances. The present invention includes each of the following embodiments:

(1) A fragrance comprising a 2-cyclohexyl-1,1-dimethyl ethanol derivative represented by formula (1)

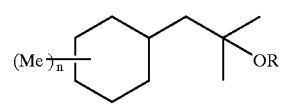
(1)

wherein R represents a hydrogen atom or an acetyl group, Me represents a methyl group, and n represents an integer from 0 to 3;

(2) A fragrance composition comprising, as an active component, a fragrance material comprising one or more types of 2-cyclohexyl-1,1-dimethyl ethanol derivatives as described in the above item (1);

(3) An aromatic bleaching composition comprising a fragrance composition described in the above item (2).

The above, and other objects, features, and advantages of the present invention will become apparent from the following description read in conjunction with the accompanying drawings, in which like reference numerals designate the same elements.

DETAILED DESCRIPTION OF THE INVENTION

Each of the following compounds are concrete examples of the 2-cyclohexyl-1,1-dimethyl ethanol derivative represented by formula (1) in each of the above described embodiments:

2-cyclohexyl-1,1-dimethyl ethanol;
2-cyclohexyl-1,1-dimethyl ethyl acetate;
2-(2-methylcyclohexyl)-1,1-dimethyl ethanol;
2-(2-methylcyclohexyl)-1,1-dimethyl ethyl acetate;
2-(3-methylcyclohexyl)-1,1-dimethyl ethanol;
2-(3-methycyclohexyl)-1,1-dimethyl ethyl acetate;
2-(4-methylcyclohexyl)-1,1-dimethyl ethanol;
2-(4-methylcyclohexyl)-1,1-dimethyl ethyl acetate;
2-(2,3-dimethylcyclohexyl)-1,1-dimethyl ethanol;
2-(2,3-dimethylcyclohexyl)-1,1-dimethyl ethyl acetate;
2-(2,4-dimethylcyclohexyl)-1,1-dimethyl ethanol;
2-(2,4-dimethylcyclohexyl)-1,1-dimethyl ethyl acetate;
2-(2,5-dimethylcyclohexyl)-1,1-dimethyl ethanol;
2-(2,5-dimethylcyclohexyl)-1,1-dimethyl ethyl acetate;
2-(2,4,6-trimethylcyclohexyl)-1,1-dimethyl ethanol; and
2-(2,4,6-trimethylcyclohexyl)-1,1-dimethyl ethyl acetate.

Among the compounds given as examples above, as well as others generically embodied in the present invention, there may be a plurality of isomers, including stereoisomers and optical isomers, based upon the methyl group substitution(s) on the cyclohexane ring. Any of these isomers, or a mixture of several of these isomers are useful in the present invention.

The above described 2-cyclohexyl-1,1-dimethyl ethanol derivatives all have a distinctive green floral scent. It has been observed that alcohols have a fresher scent nuance, and acetates have more of a rose scent nuance.

The 2-cyclohexyl-1,1-dimethyl ethanol derivatives of the present invention can be manufactured by, for example, the Grignard reaction described in Shinjikken Kagaku Kouza (published by Maruzen Corp. Ltd.), volume 14: pages 512–514, acetylation reaction described in the same, volume 14: pages 1014–1016, and hydrogenation reaction described in the same, volume 15: pages 426–428, each of which is herein incorporated by reference. Stated more concretely, the 2-cyclohexyl-1,1-dimethyl ethanol derivatives of the present invention can be manufactured by following the following reaction steps.

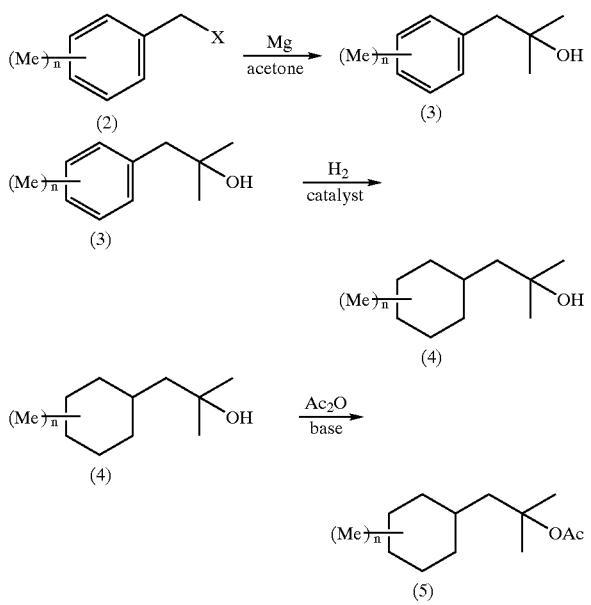

wherein Me represents a methyl group, Ac represents an acetyl group, X represents a halogen, and n is an integer from 0 to 3.

In the manufacture method for the 2-cyclohexyl-1,1-dimethyl ethanol derivative of the present invention according to the above reactions, first, a Grignard reagent, that is prepared, in an ether solvent such as tetrahydrofuran, diethyl ether, or the like, from magnesium metal and the starting substance of a halogenated benzyl, represented by general formula (2), is reacted with acetone. Normally, the reaction temperature is at −10~50° C., and preferably at 0~30° C. As a result, a benzyl alcohol represented by the general formula (3) is obtained.

Next, by reducing the resulting benzyl alcohol (3) using hydrogen gas in the presence of a hydrogenation catalyst, an alcohol compound of the present invention represented by general formula (4) is obtained. This reaction can proceed without a solvent, but alcohol solvents such as ethanol or methanol and the like, hydrocarbon solvents such as hexane or heptane and the like, ester solvents such as ethyl acetate or butyl acetate and the like can be selected and used as appropriate. Examples of hydrogenation catalysts used in this reaction include Raney® nickel, ruthenium/silica, ruthenium/alumina, rhodium/silica, rhodium/alumina, palladium/carbon, and the like. The normal reaction temperature is 0~200° C., preferably 50~150° C. The normal hydrogen pressure is about $1\times10^6$ pa~$2\times10^7$ pa, preferably about $5\times10^6$ pa~$1.5\times10^7$ pa.

Next, the alcohol represented by general formula (4) is acetylated using an acetylating reagent such as acetic anhydride or acetyl chloride and the like in the presence of a base. As a result, an acetate compound of the present invention represented by general formula (5) is obtained. This reaction proceeds without a solvent, but a hydrocarbon solvent such as hexane or heptane, a halogen solvent such as methylene chloride and the like can be selected and used as appropriate. Examples of bases used in this reaction include amine compounds such as pyridine, triethylamine and the like. The reaction temperature is normally 0–200° C., preferably 50–150° C.

In the manufacture of the compound represented by the above formula (1) of the present invention, the following compounds have 0, 1, 2, or 3 substitution groups on the cyclohexyl group: 2-cyclohexyl-1,1-dimethyl ethanol; 2-(monomethyl substituted cyclohexyl)-1,1-dimethylethanol; 2-(dimethyl substituted cyclohexyl)-1,1-dimethyl ethanol; 2-(trimethyl substituted cyclohexyl)-1,1-dimethyl ethanol; and acetates of these. When manufacturing these compounds, benzyl chloride having a substitution format corresponding to each of the compounds is used as the starting substance, and the manufacturing is conducted according to the method described above.

The 2-cyclohexyl-1,1-dimethyl ethanol derivative of the present invention represented by formula (1) all have a distinctive green floral scent and have an excellent persistent scent. Among these, the alcohols have a fresher nuance, and the acetates have more of a rose nuance.

The 2-cyclohexyl-1,1-dimethyl ethanol derivate represented by the general formula (1) of the present invention can be used alone as a scent component, or one or two or more types can be used together. Furthermore, one or more types of the 2-cyclohexyl-1,1-dimethyl ethanol derivative of the present invention represented by formula (1) and one or more types of fragrance components that are conventionally known can be mixed and used as a fragrance composition.

Conventionally known fragrances cover a wide range of fragrances. For example, components described in "Perfume and Flavor chemicals" by Arctander, S. (published by the author, Montclair, N.J. (USA) 1969) can be selected and used as appropriate. Among these, representative compounds include alpha-pinene, limonene, menthol, phenylethyl alcohol, styrallyl acetate, eugenol, rose oxide, linalool, benzaldehyde, muscone, and the like.

When preparing a fragrance composition containing as the active components fragrances comprising one or more types of 2-cyclohexyl-1,1-dimethyl ethanol derivatives of the present invention represented by formula (1), although it will depend on the objective and the types of fragrances that are used, normally the compound is mixed at from about 0.01 to about 50 weight % and preferably from about 0.1 to about 20 weight % with respect to the target fragrance composition.

The 2-cyclohexyl-1,1-dimethyl ethanol derivative of the present invention represented by formula (1) is used in various perfume products and sanitation products that require the addition of fragrances. Not only does the present invention show high stability in these base materials, but the scent can be added without losing the activity of bleaching components, such as hypochlorites, percarbonate, perborate, hydrogen peroxide, and the like.

Furthermore, the fragrance composition, containing as the active components a single fragrance comprising the 2-cyclohexyl-1,1-dimethyl ethanol derivative or a fragrance of a mixture of two or more types, can be added and used in medical products and home products including various perfume products and sanitation products. The present invention results in increased diffusivity and preservation of the scent, while, at the same time, providing a new and pleasing scent.

Stated more concretely, the present invention can be used widely in shampoos, conditioners, perfumes, colognes, hair tonics, hair creams, pomades, hair cosmetic materials, other cosmetic materials or cosmetic cleansers, room fragrances, soaps, dishwashing detergents, laundry detergents, softeners, disinfecting cleaning agents, deodorizing cleaning agents, furniture care materials, disinfectants, bacteriacidal agents, repellants, bleaching agents, and other sanitation cleaning agents, toothpaste, mouthwash, toilet paper, odor giving agents to aid in the taking of medication, and the like. It is anticipated that the addition of the fragrance composition of the present invention will increase the value of these products.

Embodiments of the present invention will be described in further detail with embodiments, but the present invention is not limited to these embodiments.

SYNTHESIS EXAMPLE 1

Synthesis of 2-Cyclohexyl-1,1-Dimethyl Ethanol 100 g (0.67 mol) of 2-phenyl-1,1-dimethyl ethanol (manufactured by Hokko Kagaku Corp. Ltd.) and 1.0 g of 5% ruthenium/silica were placed in a 500 ml stainless autoclave. The resulting mixture was placed under a hydrogen pressure of 50 atmospheres, heated to a reaction temperature of 150° C., and agitated for 5 hours. After cooling to room temperature, the catalyst was removed by filtration. Vacuum distillation of the resulting crude reaction product was conducted with a Claisen distillation device, to give 92 g of 2-cyclohexyl-1,1-dimethyl ethanol was obtained (yield: 88%, purity: 99%).

Boiling point: 60° C./ 533.2 pa. $^1$H-NMR (500 MHz, CDCl$_3$, δ) ppm:0.93–1.03 (m, 2H), 1.08–1.19 (m, 1H), 1.22 (s, 6H), 1.20–1.32 (m, 2H), 1.37 (d, J=5.6 Hz, 2H), 1.39–1.48 (m, 1H), 1.58–1.71 (m, 3H), 1.74–1.81 (m, 2H). IR(film)cm$^{-1}$: 3380, 2970, 2920 2850, 1450, 1375 MS(m/e): 141(M-15), 138, 123, 97, 83, 67, 59, 55, 43, 41, 31

SYNTHESIS EXAMPLE 2

Synthesis of 2-Cyclohexyl-1,1-Dimethyl Ethyl Acetate 50 g (0.32 mol) of 2-cyclohexyl-1,1-dimethyl ethanol, 39 g (0.38 mol) of acetic anhydride, 0.5 g (4.09 mmol) of 4-dimethyl amino pyridine, and 100 ml of pyridine were placed in a 500 ml four-necked reaction device having a thermometer and a cooling device. This was heated and agitated for 10 hours at a reaction temperature of 120° C. After cooling to room temperature and diluting with 100 ml of toluene, the resulting solution was poured into a 10% dilute hypochloric acid solution, and the aqueous layer was removed by a separating funnel. The organic layer was washed with water, neutralized, and concentrated under vacuum to provide a crude reaction product. Vacuum distillation, with a Claisen distillation device, of the crude reaction produced provided 48g of 2-cyclohexyl-1,1-dimethyl ethyl acetate (yield 76%, purity 99%).

Boiling point: 98~100° C./533.2 pa. $^1$H-NMR (500 MHz, CDCl$_3$, δ) ppm: 0.92–1.02 (m, 2H), 1.08–1.18 (m, 1H), 1.19–1.29 (m, 2H), 1.44 (s, 6H), 1.39–1.49 (m, 1H), 1.57–1.76 (m, 7H), 1.95 (s, 3H). IR (film)cm$^{-1}$: 2970, 2920, 2850, 1730, 1450, 1370, 1255 MS(m/e): 183(M-15), 141, 138, 123, 116, 101, 95, 82, 67, 59, 55, 43, 41, 29.

SYNTHESIS EXAMPLE 3

Synthesis of 2-(4-Methylcyclohexyl)-1,1-Dimethyl Ethanol (1) 5.8 g (0.21 mol) of magnesium, 50 ml of tetrahydrofuran, and 0.05 g of iodine were placed in a 500 ml four-necked reaction device having a thermometer, a cooling device, and a dropping funnel. To the resulting mixture was added, while agitating, 25.0 g (0.18 mol) of 4-methyl benzyl chloride and 150 ml of tetrahydrofuran to form a Grignard reagent. Next, while being chilled, 150 ml of a tetrahydrofuran solution of 20.7 g (0.36 mol) acetone was dropwise added over a period of 40 minutes. The resulting mixture was agitated for 5 hours at room temperature, diluted with 100 ml of hexane, poured into a 10% hypochloric acid solution, and the aqueous layer was removed by a separating funnel. The organic layer was washed with water, neutralized, and concentrated under vacuum to provide a crude reaction product. Vacuum distillation, by a Claisen distillation device, of the crude reaction product gave 22 g of 2-(4-methylphenyl)-1,1-dimethyl ethanol was obtained (yield 76%, purity 98%).

Boiling point: 100–102° C./533.2 pa. $^1$H-NMR (500 MHz, CDCl$_3$,δ) ppm: 1.22 (s,6H),2.33 (s,3H), 2.73 (s, 2H), 7.06–7.14 (m, 4H). IR (film)cm$^{-1}$: 3405, 3050, 3020, 2970, 2920, 1615, 1515, 1465, 1375, 1155, 1125. MS(m/e): 149 (M-15), 131, 106, 91, 77, 59, 43, 31.

(2) Under the same conditions as Synthesis example 1, from 19.5 g of 2-(4-methylphenyl)-1,1-dimethyl ethanol obtained from the above (1), 19.6 g of 2-(4-methylcyclohexyl)-1,1-dimethyl ethanol was obtained (yield 87%, purity 97%, isomeric ratio 73/27).

Boiling point: 91–93° C./093.3 pa. $^1$H-NMR (500 MHz, CDCl$_3$, δ) ppm: 0.82–1.04 (m, 5H), 1.23 (s, 6H), 1.15–1.85 (m, 10H). IR (film)cm$^{-1}$: 3380, 2970, 2920, 2850, 1455, 1375. MS(m/e): 155(M-15), 137, 110, 97, 81, 69, 59, 55, 43, 41, 29.

SYNTHESIS EXAMPLE 4

Synthesis of 2-(4-Methylcyclohexyl)-1,1-Dimethyl Ethyl Acetate

Under the same conditions as Synthetic example 2, from 9.4 g of 2-(4-methylcyclohexyl)-1,1-dimethyl ethanol obtained from (1) of Synthesis example 2, 8.8 g of 2-(4-methylcyclohexyl)-1,1-dimethyl acetate was obtained (yield 75%, purity 98%, isomer ratio 73/27).

Boiling point: 99–101° C./26.7 pa. $^1$H-NMR (500 MHz, CDCl$_3$, δ) ppm: 0.84–1.03(m, 5H), 1.16–1.78(m, 16H), 1.95(s, 3H). IR (film)cm$^{-1}$: 2950, 2920, 2850, 1735, 1455, 1370, 1255. MS(m/e): 197(M-15), 155, 152, 137, 116, 101, 96, 81, 67, 59, 55, 43, 41, 29.

EXAMPLE 1

Evaluation of Odor Quality

Results from odor evaluations conducted by seven expert panelist with regard to the 2-cyclohexyl-1,1-dimethyl ethanol derivatives obtained in Synthesis examples 1–4 are shown in Table 1.

Referring to Table 1, it is clear that the compounds of the present invention have a distinct green floral scent that is very pleasing.

TABLE 1

| Compound name | Scent evaluation |
| --- | --- |
| 2-cyclohexyl-1,1-dimethyl ethanol | a fresh green floral scent, the strongest scent |
| 2-cyclohexyl-1,1-dimethyl ethyl acetate | a rose green floral scent |
| 2-(4-methylcyclohexyl)-1,1-dimethyl ethanol | a fresh green floral scent |
| 2-(4-methylcyclohexyl)-1,1-dimethyl ethyl acetate | a rose green floral scent, somewhat weak |

EXAMPLE 2

Manufacture of Fragrance Composition

A mixture fragrance that is used for soap and has the following composition was manufactured by the usual methods. (recipe: the numerical units are weight parts)

TABLE 2

| | |
| --- | --- |
| geranium oil | 15 |
| patchouly oil | 15 |
| decylaldehyde | 10 |
| 10-undecenyl aldehyde | 20 |
| gamma-undecalactone | 5 |
| styrallyl acetate | 20 |
| phenyl ethyl alcohol | 150 |
| 1-citronellol | 100 |
| benzyl acetate | 50 |
| 2-methyl-3-(4-t-butylphenyl) propanal | 100 |
| eugenol | 30 |
| gamma-methyl ionone | 100 |
| alpha-(trichloromethyl) benzyl acetate | 30 |
| 3 alpha, 6,6,9 alpha-tetramethyl dodecahydronaphtho[2,1-b] furan 10% DPG solution | 5 |
| coumarin | 50 |
| 6-acetyl-1,1,2,4,4,7-hexamethyltetralin | 50 |
| | 750 |

For 750 weight parts of the mixed fragrance of Table 2, 250 weight parts of the 2-cyclohexyl-1,1-dimethyl ethanol obtained from Synthesis example 1 was added. Compared to when the compound of Synthesis example 1 was not added, it was provided with a voluminous floral green scent. Furthermore, as a result of conducting a sensing test of scent changes with the added and non-added fragrance, the fragrance that had the compound of Synthesis example 1 was found to have improved persistence of scent.

EXAMPLE 3

Manufacture of Fragrance Composition

A mixture fragrance that is used for shampoo and has the following composition was manufactured by the usual method. (recipe: the numerical units are weight parts)

TABLE 3

| | |
| --- | --- |
| lemon oil | 140 |
| orange oil | 140 |
| gamma-undecalactone | 5 |
| ethyl 2,2,6-trimethylcyclohexane carboxylate | 5 |
| allyl hexanoate | 3 |
| ethyl 2-methyl-1,3-dioxolane | 5 |
| cis-3-hexenol | 5 |
| dimethyl tetrahydrobenzaldehyde | 5 |
| phenyl ethyl alcohol | 30 |
| 1-citronellol | 100 |
| benzyl acetate | 50 |
| methyl dihydrojasmonate | 200 |
| cis-jasmone | 2 |
| 4(3)-(4-hydroxy-4-methyl pentyl)-3-cyclohexene-1-carboxyaldehyde cis-3-hexenyl salicylate | 100 |
| gamma-methyl ionone | 30 |
| 1,3,4,6,7,8-hexahydro-4,6,6,7,8,8-hexamethyl cyclopenta-gamma-2-benzopyran 50% benzyl benzoate solution | 30 |
| | 100 |
| | 950 |

To the 950 weight parts of the above mixed fragrance, 50 weight parts of 2-cyclohexyl-1,1-dimethyl ethanol obtained in Synthesis example 1 was added to prepare the fragrance composition. Compared to when the compound of Synthesis example 1 was not added, it was provided with a brilliant, lilac, floral green scent. Furthermore, as a result of conducting a sensing test of scent changes of the added and non-added fragrance, the fragrance to which the compound of Synthesis example 1 was added was found to have an improved persistence of scent.

As shown in Examples 2 and 3, the 2-cyclohexyl-1,1-dimethyl ethanol compound that is the fragrance of the present invention has a green floral scent that is lilac-like and mint-like while also being a stable compound. As a result, it can be used in various toiletries and household products. Furthermore, adding to the scent that the fragrance mixture originally possesses, the fragrance composition containing this compound can provide a green floral scent that has volume and has a bright lilac scent.

EXAMPLE 4

Manufacture of a Fragrance Composition

A mixture fragrance that is used for bleach and has the following composition was manufactured by the standard method.
(recipe: numerical units are weight parts)

TABLE 4

| | |
| --- | --- |
| lime oil | 200 |
| eucalyptus oil | 400 |
| nonyladehyde diethyl acetal | 10 |
| fenchyl alcohol | 150 |
| linalool oxide | 10 |
| ethyl 2,2,6-trimethyl cyclohexane carboxylate | 10 |
| phenyl acetaldehyde dimethyl acetal | 20 |
| | 800 |

To the 800 weight parts of the above fragrance mixture, 200 weight parts of the 2-cyclohexyl-1,1-dimethyl ethyl acetate obtained from Synthesis example 2 was added, and the fragrance composition was prepared. Compared to when it was not added, the green floral note was emphasized, and a new freesia-like scent was added. Furthermore, as a result of conducting a sensing test of scent changes of the added and non-added fragrances, the fragrance to which the compound of Synthesis example 2 was added was found to have improved persistence of scent.

EXAMPLE 5

Manufacture of Fragrance Composition

A mixture fragrance that is used for a powder detergent and has the following composition was manufactured by the standard methods.

TABLE 5

| | |
|---|---|
| orange oil | 50 |
| decylaldehyde | 5 |
| dodecylaldehyde 50% benzylbenzoate solution | 15 |
| gamma-undecalactone | 5 |
| 1-citronellyl nitrile | 10 |
| ethyl 2,2,6-trimethylcyclohexane carboxylate | 5 |
| dimethyl tetrahydrobenzaldehyde | 5 |
| allyl amylglycolate | 10 |
| dihydromyrcenol | 100 |
| isobornyl acetate | 30 |
| tricyclodecenyl acetate | 30 |
| geraniol | 200 |
| hexyl cinnamic aldehyde | 200 |
| 2-methyl-3-(4-t-butylphenyl) propanal | 150 |
| coumarin | 30 |
| 1,3,4,6,7,8-hexahydro-4,6,6,7,8,8-hexamethyl cyclopenta-gamma-2-benzopyran 50% benzyl benzoate solution galacsolide | 50 |
| 3 alpha,6,6,9 alpha-tetramethyl dodecahydronaphtho [2,1-b] furan 10% DPG solution | 5 |
| | 900 |

To 900 weight parts of the above mixture fragrance, 100 weight parts of the compound of the present invention of 2-cyclohexyl-1,1-dimethyl ethyl acetate was added to prepare the fragrance composition.

Compared to when the compound of the present invention was not added, the floral note was emphasized, providing a natural and new scent that was lilac-like. Furthermore, as a result of conducting a sensing test for the scent changes of the added and non-added fragrances, the one in which the compound of the present invention was added had an improved persistence of scent.

As indicated in Examples 4 and 5, the 2-cyclohexyl-1,1-dimethyl ethyl acetate compound of the present invention has a scent that is freesia-like, lilac-like, and rose-like, while being a stable compound. As a result, the compound of the present invention can be used in various toiletry and household products. Furthermore, with the fragrance composition containing this compound, in addition to the scent that the fragrance mixture originally possesses, a scent that emphasizes the green floral note and has a new freesia-like and a new lilac-like scent.

EXAMPLE 6

Stability Test of Various Base Materials

The 2-cyclohexyl-1,1-dimethyl ethanol obtained from Synthesis example 1 was tested for its stability in the various base materials that have been scented. It was a five level sensing evaluation test by seven expert panelist. The various scented products that were stored at 5° C. were used as controls. The results are shown in Table 6.

As is clear from Table 6, the 2-cyclohexyl-1,1-dimethyl ethanol compound was shown to be very stable in the various base materials, thereby maintaining the scent very well.

TABLE 6

| Base material | Scent ratio (%) | Storage condition | Sensing evaluation |
|---|---|---|---|
| Soap | 1.0 | 45° C./4 weeks | 5 |
| Powder detergent | 0.2 | 45° C./4 weeks | 5 |
| Softener | 0.4 | 45° C./4 weeks | 5 |
| Anti-perspirant stick | 0.5 | 45° C./4 weeks | 5 |

Evaluation levels—Compared with the controls, 5: Smells just as well; 4: The smell is somewhat weak, 3: The smell is weak; 2: The smell is very weak; 1: There is hardly any smell.

EXAMPLE 7

Bleach Stability Test

With the test recipes in Table 7 below, the chemical stability of the compound of the present invention with respect to bleaching components was evaluated by the residual chlorine concentration % of the sodium hypochlorite as well as by the masking effect of the chlorine smell compared with the non-scented product. These results were judged by a sensing evaluation by seven expert panelist. The reaction conditions were stored for four weeks in an incubation room at 40° C. The results are shown in Table 8.

TABLE 7

| (Test recipe) | | |
|---|---|---|
| NaClO solution | 5.0 wt % | (converted to amount of available chlorine) |
| NaOH | 1.0 wt % | |
| surface active agent | 3.0 wt % | |
| fragrance | 0.3 wt % | |
| distilled water | Remainder | |
| Total | 100.0 wt % | |

TABLE 8

| Fragrance | Residual chlorine concentration (%) | Sensing evaluation | Scent quality |
|---|---|---|---|
| 2-cyclohexyl-1,1-dimethyl ethanol | 100 | 5 | No change |
| 2-cyclohexyl-1,1-dimethyl ethyl acetate | 99.2 | 5 | No change |

Evaluation levels - Compared with the non-scented product, the chlorine scent is 5: not detected, 4: detected very weakly, 3: detected weakly, 2: detected somewhat weakly, 1: detected the same As is clear from Table 8, the 2-cyclohexyl-1,1-dimethyl ethanol and 2-cyclohexyl-1,1-dimethyl ethyl acetate of the present invention are very stable in bleaching agent materials. The present invention was judged to be able to mask the unpleasant chlorine smell well, without any deterioration in the active components and without any changes in the scent quality.

The 2-cyclohexyl-1,1-dimethyl ethanol derivative relating to the present invention has a distinctive green floral scent and is very pleasing and has an excellent persistence. Furthermore, fragrance compositions that have these as the active components have excellent scent properties. When these are mixed into various base materials, they show an excellent stability in the base material, and the fragrance persists over a long period of time.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A fragrance comprising a 2-cyclohexyl-1,1-dimethyl ethanol derivative represented by the formula (1)

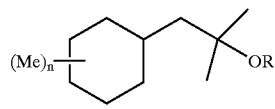

wherein R represents an acetyl group, Me represents a methyl group, and n represents an integer from 0 to 3.

2. A fragrance composition comprising:

at least one fragrance having at least one compound represented by formula (1)

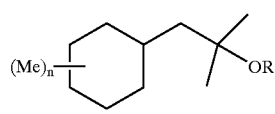

wherein R represents an acetyl group, Me represents a methyl group, and n represents an integer from 0 to 3; and a suitable carrier.

3. An aromatic bleaching composition comprising:

a bleaching agent; and a fragrance composition comprising at least one fragrance having at least one compound represented by formula (1)

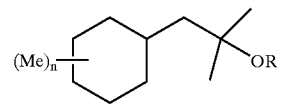

wherein R represents a hydrogen atom or an acetyl group, Me represents a methyl group, and n represents an integer from 0 to 3; and a suitable carrier.

4. A scenting method, comprising:

adding a fragrance represented by formula (1)

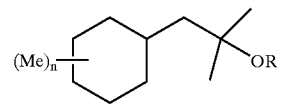

wherein R represents a hydrogen atom or an acetyl group, Me represents a methyl group and n represents an integer from 0 to 3, to a product.

5. The scenting method according to claim 4, wherein said product is selected from the group consisting of shampoos, conditioners, perfumes, colognes, hair tonics, hair creams, pomades, hair cosmetic materials, room fragrances, soaps, dishwashing detergents, laundry detergents, softeners, disinfecting cleaning agents, deodorizing cleaning agents, furniture care materials, disinfectants, bacteriacidal agents, repellants, bleaching agents, sanitation cleaning agents, toothpaste, mouthwash, toilet paper, and odor giving agents to aid in the taking of medication.

6. A sanitation product comprising the aromatic bleaching composition of claim 3.

7. A disinfecting cleaning agent comprising the aromatic bleaching composition of claim 3.

8. A laundry detergent comprising the aromatic bleaching composition of claim 3.

9. A dishwashing detergent comprising the aromatic bleaching composition of claim 3.

10. A sanitation cleaning agent comprising the aromatic bleaching composition of claim 3.

* * * * *